United States Patent [19]

Buell

[11] Patent Number: 4,900,317

[45] Date of Patent: * Feb. 13, 1990

[54] DISPOSABLE GARMENT WITH BREATHABLE LEG CUFFS

[75] Inventor: Kenneth B. Buell, Cincinnati, Ohio

[73] Assignee: The Procter & Gamble Company, Cincinnati, Ohio

[*] Notice: The portion of the term of this patent subsequent to Jan. 13, 2004 has been disclaimed.

[21] Appl. No.: 222,329

[22] Filed: Jul. 20, 1988

Related U.S. Application Data

[63] Continuation of Ser. No. 921,796, Oct. 17, 1986, abandoned, which is a continuation of Ser. No. 522,438, Aug. 11, 1983, Pat. No. 4,636,207, which is a continuation-in-part of Ser. No. 441,825, Nov. 15, 1982, abandoned.

[51] Int. Cl.$^4$ ............................................. A61F 13/16
[52] U.S. Cl. ................................ 604/370; 604/383; 604/385.2
[58] Field of Search ............... 604/366, 370, 381, 382, 604/385.1, 385.2, 394, 396

[56] References Cited

U.S. PATENT DOCUMENTS

| Re. 26,151 | 1/1967 | Duncan et al. . | |
|---|---|---|---|
| 2,545,674 | 3/1951 | Ralph | 604/394 |
| 3,156,242 | 11/1964 | Crowe, Jr. . | |
| 3,295,526 | 1/1967 | Sabee | 604/366 |
| 3,452,753 | 7/1969 | Sanford | 604/401 |
| 3,807,402 | 4/1974 | Miller et al. . | |
| 3,860,003 | 1/1975 | Buell . | |
| 3,881,488 | 5/1975 | Delanty et al. | 604/370 |
| 3,881,489 | 5/1975 | Hartwell | 604/370 |
| 3,929,135 | 12/1975 | Thompson . | |
| 3,989,867 | 11/1976 | Sisson | 604/370 |
| 4,041,951 | 8/1977 | Sanford . | |
| 4,110,508 | 8/1978 | Isgur et al. . | |
| 4,253,461 | 3/1981 | Strickland et al. . | |
| 4,276,336 | 6/1981 | Sabee . | |
| 4,280,978 | 7/1981 | Dannheim et al. . | |
| 4,306,559 | 11/1981 | Nishizawa et al. | 604/371 |
| 4,327,730 | 5/1982 | Sorensen | 604/370 |
| 4,341,216 | 7/1982 | Obenour | 604/370 |
| 4,341,217 | 7/1982 | Ferguson et al. . | |
| 4,342,314 | 8/1982 | Radel et al. . | |
| 4,386,932 | 6/1983 | Pitts . | |
| 4,425,127 | 1/1984 | Suzuki et al. | 604/369 |
| 4,425,128 | 1/1984 | Motomura . | |
| 4,427,408 | 1/1984 | Karami . | |
| 4,496,360 | 1/1985 | Joffe et al. . | |
| 4,508,256 | 4/1985 | Radel et al. . | |
| 4,515,595 | 5/1985 | Kievit et al. | 604/385.2 |
| 4,578,071 | 3/1986 | Buell . | |
| 4,597,760 | 7/1986 | Buell . | |
| 4,626,252 | 12/1986 | Nishizawa et al. . | |
| 4,636,207 | 1/1987 | Buell | 604/370 |
| 4,808,178 | 1/1989 | Aziz et al. . | |

FOREIGN PATENT DOCUMENTS

| 3319043A1 | 11/1984 | Fed. Rep. of Germany . | |
|---|---|---|---|
| 4118031 | 8/1966 | Japan . | |
| 0790062 | 2/1958 | United Kingdom | 604/397 |
| 1428572 | 3/1976 | United Kingdom . | |

Primary Examiner—C. Fred Rosenbaum
Assistant Examiner—Sharon Rose
Attorney, Agent, or Firm—Steven W. Miller; John M. Pollaro; Fredrick H. Braun

[57] ABSTRACT

Disposable diapers provided with breathable leg cuffs. Disposable diapers comprise a topsheet, an absorbent element, and a backsheet. The leg cuff of a disposable diaper is that part of the diaper which fits about the wearer's leg. Extensions of the backsheet can be used to form cuffs which are frequently elasticized. In the present invention the cuffs are formed of a material which allows passage of vapor ("breathes") while tending to retard the passage of liquid. Apertured thermoplastic films are examples of such materials. Certain advantages accrue in cuffs which are permeable to vapor in their distal portions and impermeable in the portions adjacent the absorbent element. If the disposable diaper has a breathable backsheet, the cuffs are constructed to be more permeable to vapor per unit area in their breathable portions than is the backsheet.

32 Claims, 4 Drawing Sheets

DISPOSABLE GARMENT WITH BREATHABLE LEG CUFFS

CROSS REFERENCE TO RELATED APPLICATION

This is a continuation of application Ser. No. 921,796, filed on Oct. 17, 1986 now abandoned which is a continuation of application Ser. No. 522,438, filed on Aug. 11, 1983 now U.S. Pat. No. 4,636,207; which is a continuation-in-part of application Ser. No. 441,825, filed on Nov. 15, 1982, now abandoned.

BACKGROUND OF THE INVENTION

1. Field of the Invention

This invention concerns disposable diapers, incontinent briefs, and the like.

2. Background Art

Disposable diapers are garments designed to be worn, primarily by infants, about the lower portion of the trunk and to receive discharged urine, feces, and other body fluids. Disposable diapers function to contain the discharged materials and isolate them both from the body of the wearer and from the wearer's surroundings.

For many years diapers were formed from pieces of cloth which were pinned about the lower portion of the wearer's trunk and which were intended to be laundered and reused. In more recent times, disposable diapers have come into vogue thereby freeing mothers (and others charged with the care of infants) from the distasteful task of collecting and laundering soiled cloth diapers. In addition to the logistical benefit provided by disposable diapers, modern embodiments frequently perform in a manner superior to that of cloth diapers in that they tend to present a dryer surface to the body of the wearer and tend to prevent soiling of the wearer's outer garments and other surrounding surfaces more effectively and efficiently than cloth diapers even when the latter are encased within rubber or plastic pants.

Disposable diapers, incontinent briefs, and the like normally comprise three elements: a liquid permeable topsheet intended to be placed next to the wearer's skin; a liquid impermeable backsheet which forms, in use, the outer surface of the diaper, incontinent pad, or the like; and an absorbent element interposed between the topsheet and the backsheet.

The topsheet is frequently a hydrophobic nonwoven fabric. It is readily fluid permeable so that urine will freely pass through it into the absorbent element. Its hydrophobic nature tends to cause its upper surface (i.e., the surface away from the absorbent core and, in use, adjacent the wearer's skin) to be dryer and, therefore, protected from the fluids absorbed within the absorbent element.

The absorbent element is, as its name implies, designed to receive and retain fluids which pass through the topsheet. It normally comprises layers of creped wadding or, more commonly, a batt of airlaid wood pulp fibers.

The backsheet functions to contain fluids within the absorbent element and to protect the wearer's outer garments and other surfaces from soiling by those fluids. Commonly, the backsheet comprises a fluid impermeable, vapor impermeable material such as polyethylene film.

While backsheets comprising impermeable materials do fuction to contain fluids within the absorbent core and to protect the wearer's outer garments from soiling, they are sometimes perceived as causing the diaper to be hot and uncomfortable. Further, their impermeability precludes the self-drying of the diaper which would otherwise occur because of evaporation of the fluids contained therein.

Backseets which are impermeable to liquid but permeable to vapor are known as breathable backsheets and have been described in the art. Breathable backsheets provide a cooler garment and permit some self-drying of the diaper while it is being worn. As indicated, these breathable backsheets are intended to allow the passage of vapor through them while retarding the passage of liquid. For example, U.S. Pat. No. 3,156,242, issued to Crowe, Jr. on Nov. 10, 1964, teaches the use of a microporous film as a breathable backsheet. U.S. Pat. No. 3,881,489, issued to Hartwell on May 6, 1975, teaches a breathable backsheet comprising, in combination, two layers: a low-void volume perforated thermoplastic film and a porous high-void volume hydrophobic tissue. U.S. Pat. No. 3,989,867, issued to Sisson on Nov. 2, 1976, teaches a breathable backsheet provided with tapered hollowed bosses which prevent the passage of liquids while allowing vapors to pass readily therethrough. (These three patents are incorporated herein by reference.)

As a general matter, the last two cited patents, provide for breathability across substantially the entire outer surface of the diaper. U.S. Pat. No. 4,341,216, issued to Obenour on July 27, 1982, incorporated herein by reference, describes and claims a somewhat different exemplary breathable backsheet. One practical effect of this invention is to tend to restrict the vapor permeability of the breathable backsheet in the crotch region relative to the vapor permeability of the backsheet in the waist regions.

While breathable backsheets do provide an improvement over the more common impermeable backsheets, and while those described in the last three mentioned patents are of particular value, developments providing for more comfortable and more serviceable diapers have still been sought.

SUMMARY OF THE INVENTION

The present invention is of disposable diapers comprising breathable cuffs or, in other terms, cuffs which allow the passage of vapor through them.

The cuff (or leg band) of a disposable diaper is that portion of the diaper which, in use, wraps about and contacts the leg of the wearer, normally in the region of the wearer's thigh. The cuff is normally, although not necessarily, a part or extension of the backsheet; it can be a part or extension of the topsheet or even a separate element attached or affixed to the diaper. A breathable cuff is one which allows the more or less free passage of vapor (including air and water vapor) through it while resisting the passage of liquid to a greater or lesser degree. A disposable diaper normally has two cuffs.

The cuffs can be breathable over their entire extent (or surface) or they can be breathable over only a portion of their extent.

DETAILED DESCRIPTION OF THE INVENTION

While this specification concludes with claims particularly pointing out and distinctly claiming the subject matter regarded as the invention, it is believed that a better understanding of the invention can be achieved through careful reading of the following detailed description of the invention in conjunction with study of the attached drawings and appended example.

The present invention is of a distinct improvement in disposable diapers, incontinent briefs, and the like.

Disposable diapers have heretofore been presented in a variety of embodiments; it is intended that the present invention be used in conjunction with the various known embodiments. In particular, U.S. Patent Re 26,151 which was issued to Duncan and Baker on Jan. 31, 1967, describes and claims a disposable diaper which has achieved wide acceptance and commercial success. U.S. Pat. No. 3,860,003, which was issued to Buell on Jan. 14, 1975, describes and claims significantly improved disposable diapers which, too, have achieved wide acceptance and commercial success. The diaper taught by Buell differs from that taught by Duncan and Baker in many respects, not the least of which is the provision in the Buell diaper of a contractible leg opening having a side flap which is of sufficient width and flexibility to provide continued non-slipping contact with the wearer's body thereby providing improved containment of fluids. In the terminology of the present specification, the Buell diaper can be said to have elastic cuffs.

A still different embodiment of a disposable diaper was described and claimed by Aziz and Blaney in European Patent Application No. 82200801.7, filed June 29, 1982. The Aziz and Blaney diaper also differs from the Duncan and Baker diaper in many respects, not the least of which is the provision of a multiplicity of flaps which fit about the legs of the wearer when the diaper is worn and which have a fixed edge connected to the outer covering layer and an elasticized distal edge spaced from the fixed edge. As with the Buell diaper, in the terminology of the present specification, the Aziz and Blaney diaper can be said to have contractible or elastic cuffs.

Another form of disposable diaper (sometimes referred to as an incontinent brief and intended to be worn by adults) is shown in U.S. Pat. No. 4,253,461 issued to Strickland and Visscher on Mar. 3, 1981.

The immediately foregoing four patents and the European patent application are incorporated herein by reference.

For convenience of description, the present invention shall be described as applied to the Aziz and Blaney diaper. It is to be understood, however, that the present invnetion can be used, and is recommended for use, with other disposable diaper embodiments, particularly that described by Buell.

Figure 1:
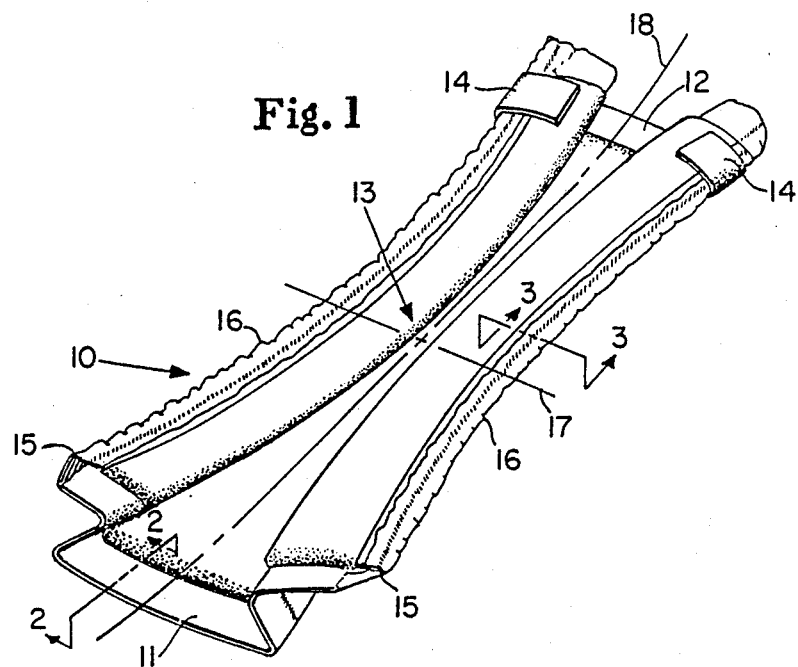
FIG. 1 is a perspective view of a disposable diaper in Z-folded configuration ready to be placed on an infant; it represents a disposable diaper with which the present invention can beneficially be used.

FIG. 1 is a perspective view of a disposable diaper 10 (after Aziz and Blaney) which is Z-folded and ready to be placed on an infant. In general, crotch portion 13 of diaper 10 is placed between the wearer's legs and front waist portion 11 and back waist portion 12 are place, respectively, adjacent the wearer's front and back waist areas. Front waist portion 11 and back portion 12 are joined by adhesive attachment tapes 14 so as to encircle the wearer's waist and hold diaper 10 in place.

Diaper 10 is generally symmetrical about lateral center line 17 which runs laterally across its width. It is also symmetrical about longitudinal center line 18 which runs longitudinally along its length. In a symmetrical disposable diaper, the designations "front" and "rear" in conjunction with front waist portion 11 and rear waist portion 12 are induced by the location of adhesive attachment tapes 14.

The cuffs of disposable diaper 10 are indicated by reference numeral 15. In FIG. 1, cuffs 15 are shown as generalized representations of cuffs, certain embodiments of which are breathable and which will be described with more particularity hereinafter. Cuffs 15 can be and sometimes are referred to as leg bands or side flaps without doing undue violence to terminology. Cuffs 15 have longitudinal side margins 16 on their respective outboard edges.

As noted in the Background Art section of this specification, disposable diapers comprise three main elements: a topsheet, a backsheet, and an absorbent element. Disposable diaper 10 as shown in FIG. 1 is no exception. While disposable diaper 10 contains additional elements as hereinafter described, it does comprise the three basic elements of disposable diapers.

Figure 2:
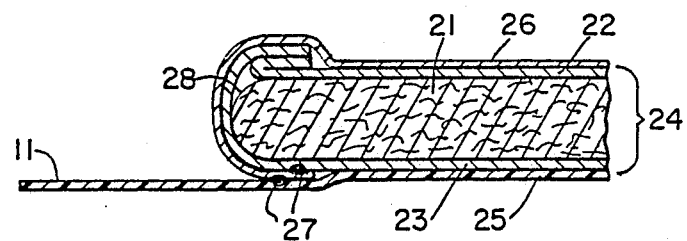
FIG. 2 is a cross sectional view of the diaper of FIG. 1 taken along line 2—2 and illustrates an aspect of its construction.

In FIG. 2, as in the other figures depicting cross sectional views, the thickness of certain materials has been exaggerated for clarity. Further, in all of the figures, reference numerals are used consistently to identify the same or similar elements.

FIG. 2 is a cross sectional view of disposable diaper 10 taken along line 2—2 in front waist portion 11. It illustrates an aspect of the construction of diaper 10.

The major elements of disposable diaper 10 are topsheet 26, absorbent element 24, and backsheet 25. Top envelope tissue 22 and back envelope tissue 23 are placed adjacent absorbent core 21 to enclose absorbent core 21, to contain the materials from which it is constructed, and to lend it tensile strength. The combination of top envelope tissue 22, absorbent core 21, and back envelope tissue 23 is considered to be an absorbent element as indicated by reference numeral 24. That is to say, the three components function generally as a unitary absorbent element.

Figure 3:
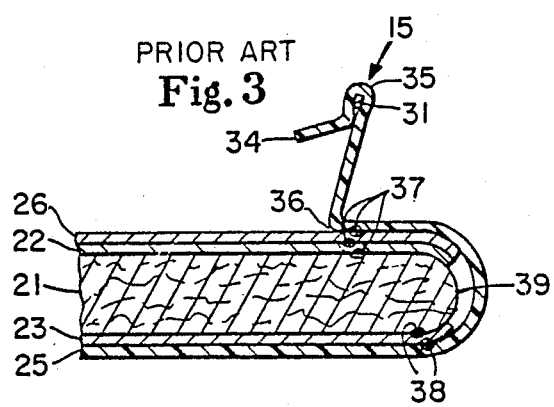
FIG. 3 is a cross sectional view of the diaper of FIG. 1 taken along line 3—3 and illustrates the cuff construction of a prior art diaper.

In the particular embodiment of disposable diaper 10 under discussion, absorbent core 21 is a generally planar, generally rectagular, absorbent body. Top envelope tissue 22 and back envelope tissue 23 are essentially co-extensive with absorbent core 21 and are placed adjacent its opposed faces. As indicated in FIG. 2, back envelope tissue 23 is folded up and about lateral end margin 28 of absorbent core 21 in the waist portion of disposable diaper 10 and is secured to top envelope tissue 22 by means not illustrated. (Envelope tissues 22 and 23, as shown in FIG. 3, for example, do not overlap longitudinal side margins 39 of absorbent core 21.) The construction of diaper 10 in rear waist portion 12 is similar to that shown in FIG. 2. The repective sizes of envelope tissues 22 and 23 are dictated by the size of absorbent core 21.

Envelope tissues 22 and 23 can be made from any permeable material well known to those skilled in the art. Preferably, the materials possess wet strength characteristics. Particularly satisfactory results are obtained when envelope tissues 22 and 23 are constructed from sheets of wet strength tissue paper having a basis weight of about 16 grams per square meter and having an air permeability of about 30.5 cubic meters per minute per square meter ($M^2$) of tissue at a pressure differential of about 12.7 millimeters of water.

In the context of disposable diapers, envelope tissues such as top envelope tissue 22 and back envelope tissue 23 are optional elements. While not required, their presence is preferred.

Envelope tissues 22 and 23 can optionally be secured to the respective faces of absorbent core 21 by any convenient means (not shown) well known to those skilled in the art.

Absorbent core 21 can be any means which is generally compressible, conformable, non-irritating to the wearer's skin, and which is capable of absorbing and retaining fluids.

In the embodiment illustrated, absorbent core 21 is rectangular in shape. Its lateral and longitudinal dimensions are selected depending on the size of the infant selected to wear the disposable diaper. When disposable diaper 10 is selected for wear by an infant weighing from about 5 to about 10 kilograms, absorbent core 21 is about 31.8 centimeters (cm) wide (lateral dimension) by about 40.6 centimeters long (longitudinal dimension). Other sizes for larger or smaller infants can be readily selected by those skilled in the art.

Absorbent core 21 can be constructed from any of a variety of materials commonly used in disposable absorbent articles and which are described in the hereinbefore incorporated patents. Examples of suitable absorbent materials include creped cellulose wadding, absorbent foams, absorbent sponges, super absorbent polymers, and, preferably, comminuted and airlaid wood pulp commonly referred to as absorbent fluff. In an embodiment of the size hereinbefore mentioned, when absorbent core 21 comprises absorbent fluff, absorbent core 21 weighs from about 30 to about 56 grams (g) and has an absorbent capacity of from about 8 to about 16 grams of water per gram of absorbent fluff. It has a density of from about 0.10 to about 0.175 grams per cubic centimeter.

The second major element of disposable diaper 10, as illstrated in FIG. 2, is topsheet 26. Topsheet 26 is secured to back envelope tissue 23 and backsheet 25 by, respectively, securement means 27. Securement means 27 can be any means well known to those skilled in the art such as adhesive attachment. A suitable adhesive is the hot melt adhesive sold under the trademark Eastobond A-3 by Eastman Chemical Products Company, Kingsport, Tenn.

Topsheet 26 can be any compliant, soft feeling, non-irritating (to the wearer's skin), liquid permeable, planar material. It can be constructed of porous paper made from natural or synthetic fibers or mixtures thereof, nonwoven fabric made from natural or synthetic fibers or mixtures thereof, apertured plastic film, porous foam, or the like. Examples of suitable topsheets are described, for example, in the hereinbefore incorporated patents of Duncan and Baker and Buell.

A diaper topsheet functions to contact the wearer's skin, to receive fluid discharges, to allow the discharges to pass rapidly therethrough into the absorbent core, and to isolate the wearer's skin from the fluids in the absorbent core. To aid in effective performance of the last function, the topsheet is preferably hydrophobic.

A preferred topsheet is spun-bonded nonwoven polyester fabric made from fibers of from about 2.2 to about 2.5 denier, having a basis weight of about 17 grams per square meter. Another preferred topsheet material comprises about 65% staple length, 1.5 denier polyester fibers (such as Kodel type 411 polyester fibers as sold by Tennessee Eastman Corporation, Kingsport, Tenn. ); about 15% crimped, staple length, 1.5 denier rayon fibers; and about 20% acrylic copolymer binder (such as Celanese CPE 8335, as sold by Celanese Corporation of Charlotte, N.C). "Staple length" refers to fibers having a length of at least about 15 millimeters (mm).

Suitable topsheets can also be constructed from apertured plastic films such as those described by Radel and Thompson in U.S. Pat. No. 4,342,314, issued Aug. 3, 1982 and incorporated herein by reference. Another apertured thermoplastic film useful as a topsheet is described with particularity in U.S. Pat. No. 4,341,217 issued to Ferguson and Landrigan on July 27, 1982, which patent is also incorporated herein by reference. A still further suitable topsheet can be formed from a liquid impermeable material provided with tapered capillaries as described in U.S. Pat. No. 3,929,135, issued to Thompson on Dec. 30, 1975 and incorporated herein by reference.

Another preferred topsheet is constructed from polypropylene fibers which have been carded and thermally bonded in a spaced-apart pattern. Fibers about 3.8 cm long and of from about 1.5 to about 3.0 denier are suitable. A preferred sheet has a basis weight of about 22 grams per square meter.

The size of topsheet 26 is dictated by the size of absorbent core 21.

Disposable diapers commonly and preferably have topsheets. It is not unknown, however, for disposable diapers to be constructed without a topsheet (as, for example, when the surface of the absorbent element serves the function of a topsheet). The present invention will function in such a structure and its use therein is contemplated.

As discussed hereinbefore, one function of backsheet 25 is to prevent fluids from escaping from disposable diaper 10 and soiling the wearer's outer garments or other surfaces in contact with the disposable diaper. Any compliant, non-irritating, planar material which is impermeable to fluid body discharges can be used as backsheet 25. Suitable materials are described with particularity in, for example, the hereinbefore incorporated patents to Duncan and Baker and to Buell.

A preferred backsheet is formed from polyethylene film having a thickness of from about 0.012 to about 0.051 millimeter.

Breathable backsheets useful in the present invention are described in the hereinbefore mentioned patents to Crowe, Jr., Hartwell, Sisson, and Obenour.

The size of backsheet 25 is dictated by the size of absorbent core 21 and the exact diaper design selected.

As will be discussed more fully hereinafter, the present invention involves breathable cuffs on disposable diapers. In certain preferred embodiments of this invention, the breathable cuffs can be constructed from a portion of backsheet 25. This requires that certain modifications be made to the longitudinal margins of backsheet 25. Thus, the discussion of backsheets (including backsheet 25) up to this point in this specification can properly be considered to refer to that portion of backsheet 25 which forms the outer portion of the disposable diaper (including disposable diaper 10). That is to say, that portion of the backsheet extending from and including front waist portion 11 to and including rear waist portion 12 in the longitudinal direction and between cuffs 15 in the latitudinal direction is considered to be the backsheet proper of a disposable diaper.

In FIG. 1, cuffs 15 as illustrated are generalized representations of cuff portions. They are defined more specifically by reference to cross sections of cuff 15 taken along line 3—3.

FIG. 3 is an enlarged cross sectional view of cuff 15 taken along line 3—3 of FIG. 1 and illustrates a prior art elasticized cuff.

Top envelope tissue 22, back envelope tissue 23, and topsheet are essentially coterminous with longitudinal side margin 39 of absorbent core 21. Topsheet 26 is preferably secured to top envelope tissue 22 which in turn can be optionally secured to absorbent core 21 by securement means 37. Securement means 37 can be any means well known to those skilled in the art such as adhesive attachment. Backsheet 25 is folded about longitudinal side margin 39 of the absorbent core 21 as illustrated and is secured to topsheet 26 by securement means 37. Optionally, backsheet 25 and back envelope tissue 23 can be secured to absorbent core 21 by optional securement means 38 which can be any means well known to those skilled in the art, such as adhesive attachment.

Attaching backsheet 25 to topsheet 26 with securement means 37 provides a fixed edge 36 for cuff 15. The extension of backsheet 25 from fixed edge 36 through distal edge 35 of cuff 15 to free end 34 serves to form cuff 15.

In the prior art embodiment shown in FIG. 3, elastic element 31 is operably associated with cuff 15 by securing it to cuff 15 with elastic attachment means which are not shown. The elastic attachment means should be flexible and of sufficient adhesiveness to hold elastic element 31 in its stretched condition substantially indefinitely. A suitable means is a hot melt adhesive such as that marketed by Findley Adhesives Incorporated, Elmgrove, Wisconsin, under the trademark Findley Adhesives 691-336. A more detailed description of the manner in which elastic element 31 should be positioned and secured to disposable diaper 10 is given in the hereinbefore incorporated patent to Buell. It should also be noted that one or several elastic elements can be used in the elastic cuffs of disposable diapers.

Elastic element 31 is affixed to cuff 15 in an elastically contractible condition so that in a normally unrestrained configuration, elastic element 31 effectively contracts or gathers the cuff material adjacent elastic element 31. Elastic element 31 can be affixed to cuff 15 in an elastically contractible condition in at least two ways. For example, elastic element 31 may be stretched to a stretched condition and fixed to cuff 15 while cuff 15 is in an uncontracted condition. Alternatively, cuff 15 may be contracted, for example by pleating, and elastic element 31 fixed to the contracted cuff 15 while elastic element 31 is in its relaxed or unstretched condition.

Preferably, elastic element 31 develops a skin contact pressure in use of from about 0.007 to about 0.17 kilogram per square centimeter. To provide the proper skin contact pressure, elastic element 31 will preferably have a contractual force in its stretched condition of from about 10 to about 200 grams. Elastic element 31 should provide such a contractional force and thus establish its stretched condition at an elongation from its relaxed state of from about 50 to about 400%. One elastic element which has been found to be suitable is an elastic tape having a cross section of 0.18 millimeter by 1.5 millimeter and made from natural rubber as available from East Hampton Rubber Company of Stuart, Va., under the trademark L-1900 Rubber Compound. Other suitable elastic elements can be made from natural rubber elastic tapes sold under the trademark Fulfex 9211 by Fulflex Company of Scotland, N.C. The length of elastic element 31 in general is dictated by diaper design. In the embodiment illustrated in FIG. 1, elastic element extends essentially the entire length of cuff 15.

Cuff 15 is constructed from flexible material. The overall width of cuff 15 can be considered to be the distance from fixed edge 36 to distal edge 35 when cuff 15 is fully extended. Because cuff 15 is flexible, the actual distance, in use, between the disposable diaper as typically represented by the outer surface of topsheet 26 and distal edge 35 can vary.

Typically, the width of cuff 15 is greater than about 6.3 millimeters. Preferably, this width will be at least about 13 millimeters and more preferably at least about 19 millimeters. The maximum width of cuff 15 will be determined by practical considerations of diaper size and material cost.

The dimension of cuff 15 from distal edge 15 to free end 34 will vary according to diaper size and design.

The length of cuff 15 (i.e., its dimension along the longitudinal margin of disposable diaper 10) will vary according to diaper size and design. In the embodiment shown in FIG. 1, cuff 15 extends essentially the entire length of diaper 10.

As has been noted hereinbefore, the present invention is of a significant improvement in disposable diapers. The discussion heretofore in this specification has been primarily of prior art diapers and was necessary to fully describe the context in which the present invention is used. Attention shall now be directed more specifically to the present invention.

As shown in the prior art embodiment illustrated in FIG. 3, cuff 15 is of an impermeable material. Even if the major portion of backsheet 25 is a breathable backsheet, that portion of the backsheet which forms the diaper cuff (or the longitudinal margins) is nonbreathable (i.e., impermeable to both liquid and vapor). In the present invention, cuff 15 is permeable to vapor over at least a portion of its surface or extent. (In this specification "breathable" is used to describe a material or element which is "permeable to vapor." The two terms can be and are used interchangeably.)

Figure 4:
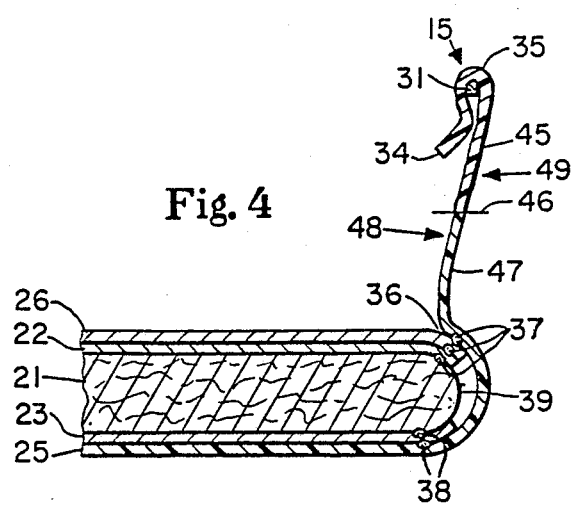
FIG. 4 is a cross sectional view of an embodiment of the present invention taken along a line corresponding to line 3—3 of FIG. 1.

Referring to FIG. 4, imaginary line of demarcation 46 represents the transition between breathable (vapor permeable) and impermeable zones of cuff 15. Reference numeral 47 indicates generally the impermeable portion of cuff 15 while reference numeral 45 indicates generally the breathable portion of cuff 15. The precise location of imaginary line of demarcation 46 is not fixed but is, rather, selected by the diaper designer to provide the desired performance. If imaginary line of demarcation 46 is established adjacent fixed edge 36, essentially all of cuff 15 will be breathable. If, however, imaginary line of demarcation 46 is established adjacent distal edge 35, cuff 15 will be effectively nonbreathable and will be functionally equivalent to prior art cuffs.

As indicated by the differences in shading in FIG. 4, breathable portion 45 of cuff 15 is different in character from impermeable portion 47 of cuff 15. In the simplest case, impermeable portion 47 is impermeable to both liquid and vapor. (It is recognized that virtually all sheet materials have some finite, albeit sometimes small, permeability to vapor and, under certain pressures, liquid. As used in this specification, "impermeable," whether referring to vapor or liquid, means that the material under discussion is substantially resistant to the passage of vapor or liquid in a practical sense in the context of disposable diapers. Likewise "permeable" is used to describe a material which allows the readily measurable passage of liquid or vapor, as the case may be, under the conditions normally prevailing during the use of disposable diapers.) Breathable portion 45, in the simplest case, is freely permeable to both vapor and liquid.

In a more complex and practical situation, impermeable portion 47 is, as before, impermeable to both liquid and vapor while breathable portion 45 is relatively permeable to vapor but relatively impermeable to liquid.

In a still more complex situation, as when backsheet 25 of disposable diaper 10 is a breathable backsheet, impermeable portion 47 will be relatively impermeable to liquid and permeable to vapor while breathable portion 45 will be relatively more permeable to vapor per unit area than is impermeable portion 47 or backsheet 25.

The overall breathability of cuff 15 (that is to say, the amount of air and moisture vapor which can be transported through breathable portion 45 in any given length of time under any given conditions) can be varied and controlled by adjustment of a number of factors. Among these are the inherent permeability of the material used to construct breathable portion 45, the physical length and width of breathable portion 45, and the location of imaginary line of demarcation 46 to delineate the relative sizes of breathable portion 45 and impermeable portion 47.

Breathability of cuff 15 will be greatest, all other conditions being constant, when breathable portion 45 is at a maximum and impermeable portion 47 is at a minimum (i.e., nonexistant). As a practical matter, it is not necessarily preferable to have cuff 15 totally breathable.

In general, if breathable portion 45 is constructed of a material which allows free passage of vapor, it will also allow some finite, greater or lesser, passage of liquid. It is desirable to maintain this passage of liquid (termed "leakage" in the art) at some minimum value determined by consumer acceptance. It has been surprisingly discovered that a desirable balance between breathability and leakage can be maintained if impermeable portion 47 has some finite value. While the inventor does not wish to be bound by any theory of operation, it appears that this balance is achieved through a gasketing function performed by impermeable portion 47.

Since cuff 15 is flexible, it can assume an infinite number of orientations relative to absorbent core 21. If cuff 15 is considered to be oriented relative to absorbent pad 21 as shown in FIG. 4, cuff 15 can be said to have an inner surface 48 and an outer surface 49. Inner surface 48 of cuff 15 will be that surface generally oriented toward the body of the diaper and absorbent pad 21. Outer surface 49 is the surface of cuff 15 opposite the inner surface 48. In use, as diaper 10 is applied to the body of the infant with crotch portion 13 generally in the infant's crotch region and as front waist portion 11 and rear waist portion 12 are brought about the infant's waist, cuffs 15 are brought adjacent the inner and outer aspects of the infant's thighs. Cuffs 15 tend to rotate to a greater or lesser degree in the direction of outer surface 49 thereby bringing inner surface 48 into contact with the infant's skin. While the major portion of contact between cuff 15 and the infant's skin is induced by and is in the region of elastic element 31, other portions of inner surface 48 of cuff 15 will tend to be brought into contact with the infant's skin. This includes the inner surface of impermeable region 47. Any liquid which leaks from the diaper proper, as from absorbent core 21, must approach cuff 15 from the direction of the diaper proper and in the direction of inner surface 48. If inner surface 48 of impermeable portion 47 is adjacent to the infant's thighs (either in touching relationship or merely in close proximity), a significant portion of the liquid tending to leak from the diaper will contact impermeable portion 47 and will be redirected into absorbent pad 21 generally through topsheet 26 and top envelope tissue 22. Thus, having impermeable portion 47 in addition to breathable portion 45 tends to limit leakage.

Providing at least inner surface 48 of breathable portion 45 with such characteristics as will retard the passage of liquid without unduly hindering the passage of vapor will likewise tend to redirect liquid into absorbent core 21 as does impermeable portion 47. Physical characteristics tending to retard the passage of liquid include the hydrophobicity of inner surface 48 of breathable zone 45 as well as physical construction of breathable zone 45 so as to provide it with "one-way apertures." One-way apertures are discussed in detail in the aforementioned patents to Thompson, Ferguson and Landrigan, and Radel and Thompson. A thermoplastic film provided with apertures having a diameter of less than about 0.13 millimeter, preferably less than about 0.02 millimeter, also tends to allow the passage of vapor while retarding the passage of liquid.

Preferably, permeable portion 45 constitutes from about 5% to about 75% of the width of cuff 15.

Preferably, breathable portion 45 extends the entire longitudinal length of cuff 15, although in certain embodiments it can be restricted to that portion of cuff 15 falling within the scope of crotch portion 13. As a practical matter, even if breathable portion 45 extends the entire length of cuff 15, it will essentially have an effective length essentially equivalent to the length of contact between cuff 15 and the infant's thigh. In certain diaper designs, portions of breathable portion 45 outside crotch portion 13 will tend to be occluded by backsheet 25 as diaper 10 is secured to the infant.

Breathable portion 45 and impermeable portion 47 of cuff 15 can be constructed in any suitable way.

Figure 8:
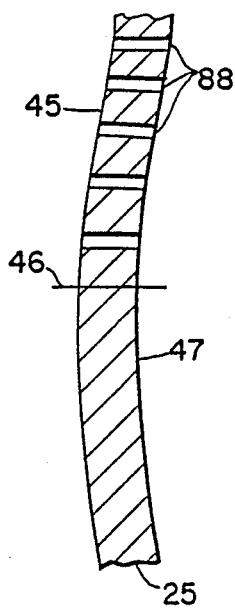
FIG. 8 is an enlarged fractional view of one embodiment of the present invention.

For example, in FIG. 4, cuff is shown to be formed as an integral extension of backsheet 25. That is to say, cuff 15 is formed unitarily with backsheet 25. Breathable portion 45 is obtained, for example, by aperturing in selected regions the thermoplastic film used to form backsheet 25. If backsheet 25 is formed from a rectangular section of thermoplastic film having a lateral width and a longitudinal length, the areas selected for aperturing will be those areas adjacent the longitudinal edges of the sheet and running along the longitudinal edges. For example, if backsheet 25 is constructed from polyethylene film having a lateral width of about 40 centimeters, it can be apertured in zones adjacent each longitudinal edge for a distance extending laterally about 7.6 centimeters from each longitudinal edge toward the imaginary longitudinal center line. FIG. 8 is a fragmentary enlarged view of the cross section of cuff 15 in the region of imaginary line of demarcation 46 and illustrates the method of construction just described. Impermeable portion 47 is shown on one side of imaginary line of demarcation 46 and breathable portion 45 is shown on the other side of the line. Generalized apertures 88 are shown extending through the material comprising breathable portion 45.

Figure 9:
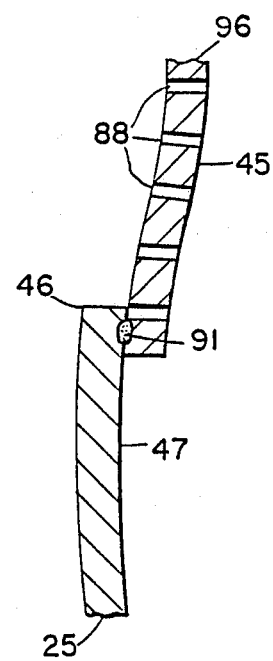
FIG. 9 is an enlarged fractional view of an alternate embodiment of the present invention.

Alternatively, backsheet 25 can be constructed in such a way as to completely encase the outer surface of disposable diaper 10 as indicated in the drawings and provide sufficient excess material integral with backsheet 25 to construct those portions of cuffs 15 up to imaginary lines of demarcation 46. A breathable cuff sub-element, which can be an apertured film or another breathable material, is then affixed to backsheet 25 in the region of imaginary line of demarcation 46 in such a manner as to form breathable portion 45 of cuff 15. FIG. 9 illustrates this method of construction in a fragmentary enlarged view of the cross section of cuff 15 in the region of imaginary line of demarcation 46. In FIG. 9, breathable cuff sub-element 96 is shown provided with generalized apertures 88 and affixed to impermeable portion 47 of cuff 15 (as formed from backsheet 25) in lapping relationship by securement means 91 which can be any convenient means known to those skilled in the art, such as adhesive attachment. It should be emphasized that breathable cuff sub-element 96, while represented in FIG. 9 as an apertured film, can be any suitable breathable material, such as topsheet material.

Impermeable portion 47 and breathable portion 45 are essentially extensions of backsheet 25 when either method of construction (as shown in FIGS. 8 and 9) is used. Thus, FIG. 8 represents a cuff and backsheet which are formed of an integral material while FIG. 9 represents a cuff and a backsheet formed of a composite material which performs as an integral material.

In all of the embodiments of the present invention illustrated in this specification, impermeable portions 47 are formed from an integral part of backsheet 25. While this method of construction is preferred, embodiments wherein the backsheet and the impermeable portions of the cuffs are constructed of separate elements (and perhaps of different materials) are included within the scope of the present invention.

A method of aperturing materials to provide breathable portion 45 can readily be selected by those skilled in the art from techniques and designs known to the art. For example, if backsheet 25 is a thermoplastic film (such as common polyethylene film) it can be apertured to provide breathable zone 45 to a degree which can be described in terms of a dimensionless R value defined as $$R = \frac{D(OA)}{C}$$

wherein D is the average diameter (in centimeters) of the apertures in the film, OA is the total open area of the apertured film expressed as a percentage, and C is the average caliper (or length or height) of the apertures (in centimeters). Normally, when apertures are formed in an elastic film, they take the form of somewhat irregular cones open at both apex and base. Average diameter is the arithmetic average of the diameters of the two openings so formed. Of course, if the apertures are uniformly cut from the film without the usual formation of the cones, caliper will be the film thickness. An apertured film having an R value of between about 2 and about 40, preferably between about 5 and about 25, usually has a vapor transfer rate suitable for use in the present invention. Apertured films described in the hereinbefore incorporated patents to Sisson, Ferguson and Landrigan, Thompson, and Hartwell can also be used.

If elastic element 31 is attached to cuff 15 by ultrasonic welding, apertures can conveniently be formed in breathable portion 45 by ultrasonic means concurrently with the welding. Naturally, apertures can be formed in breathable portion 45 by ultrasonic means separate and apart from any welding. In the drawings, the elastic elements are shown to be in the nature of bands. These elements can also comprise thin elastic films which can occupy a large portion of the cuff area. In this design, it is frequently advantageous to provide the elastic films with perforations or apertures. The use of ultrasonic energy is also useful in this regard.

Figure 5:
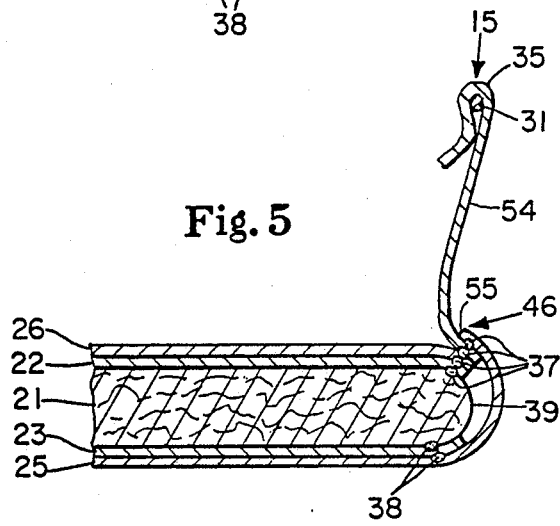
FIG. 5 is a cross sectional view of an alternate embodiment of the present invention taken along a line corresponding to line 3—3 of FIG. 1.

An alternate embodiment of cuff 15 is illustrated in FIG. 5, which is, as are FIGS. 3 and 4, a cross section of generalized cuff 15 of disposable diaper 10 of FIG. 1 taken along line 3—3. In this embodiment, backsheet 25 encloses longitudinal margin 39 of absorbent core 21 and is secured indirectly to topsheet 26 by securement means 37. Backsheet 25 terminates adjacent securement means 37 at backsheet longitudinal edge 55. As illustrated in FIG. 5, breathable element 54 is attached intermediate topsheet 26 and backsheet 25 by securement means 37 adjacent backsheet longitudinal edge 55. (In the embodiment shown in FIG. 5, breathable element 54 is attached intermediate topsheet 26 and backsheet 25. In an alternate, but less preferred embodiment, breathable element 54 can be affixed indirectly to topsheet 26 with backsheet 25 interposed between breathable element 54 and topsheet 26.) Cuff 15 is then constructed from breathable element 54 in a manner analogous to that in previously described embodiments, including attachment to elastic element 31. In this embodiment, breathable element 54 constitutes the whole of the breathable portion. Imaginary line of demarcation 46, in this embodiment, corresponds with backsheet longitudinal edge 55.

While breathable element 54 can be an apertured film as described in connection with other embodiments, it preferably is a nonwoven fabric such as that used to construct topsheet 26. Constructing cuff 15 essentially completely from nonwoven fabric as shown in this embodiment provides two benefits: breathability and comfort. The breathability aspect has been extensively discussed herein before. The comfort aspect accrues from the interposition, in use, of breathable element 54 (which is constructed from nonwoven fabric) between backsheet 25 (which commonly is constructed of a plastic film) and the wearer's skin. Thus, direct contact between plastic and skin is eliminated.

Figure 6:
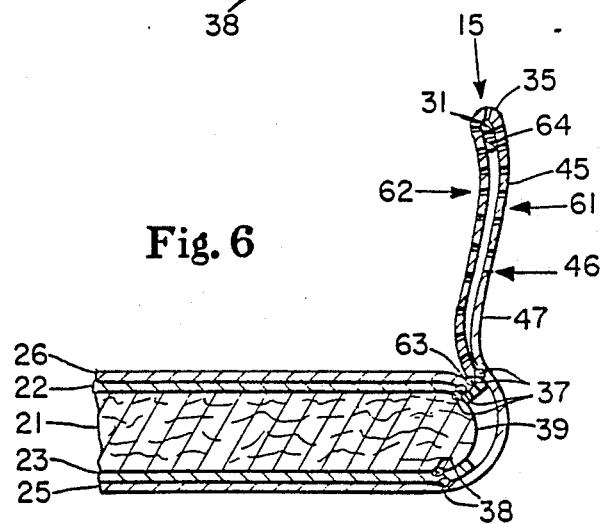
FIG. 6 is a cross sectional view of an alternate embodiment of the present invention taken along a line corresponding to line 3—3 of FIG. 1.

An alternate embodiment of cuff 15 is illustrated in FIG. 6, which is, as are FIGS. 3, 4 and 5, a cross section view of generalized cuff 15 of disposable diaper 10 of FIG. 1 taken along line 3—3. In this embodiment, cuff 15 is constructed essentially as the embodiment shown in FIG. 4 up to distal edge 35. That is to say, backsheet 25 and cuff 15 (up to distal edge 35) are constructed essentially of an integral material or of a composite material which performs as an integral material. The transition between impermeable portion 47 and permeable portion 45 is indicated by imaginary line of demarcation 46. Beyond imaginary line of demarcation 46, cuff 15 is constructed of apertured film as hereinbefore described. The apertured film extends from imaginary line of demarcation 46 to distal edge 35 and is folded about elastic element 31 and second elastic element 64. (In this embodiment two elastic elements are shown: elastic element 31 and second elastic element 64. Second elastic element 64, the use of which is optional, is similar to elastic element 31 in construction.) In embodiments previously described, the elastic elements preferably extend in cuffs 15 essentially the entire longitudinal length of the diaper from front waist portion 11 to rear portion 12. In this particular embodiment, elastic element 31 and second elastic element 64 preferably extend throughout the major portion of the length of cuff 15, but terminate at some point between front waist portion 11 and lateral center line 17 at one end and between rear waist portion 12 and lateral center line 17 on the other end. Preferably, the two elastic elements extend from lateral center line 17 toward each waist portion a distance of from about 50% to about 80% of the total distance between lateral center line 17 and the respective waist portion.

From distal edge 35, the apertured film is folded about elastic element 31 and second elastic element 64 and secured thereto by means not shown in the figure but well known to those skilled in the art. The apertured film is then secured to topsheet 26 intermediate topsheet 26 and impermeable portion 47 at inner attachment point 63. Backsheet 25 is indirectly secured to topsheet 26 with securement means 37.

In this embodiment, the apertured and unapertured materials comprising cuff 15 form a loop having an outer face section 61 and an inner face section 62. Outer face section 61 and inner face section 62 are essentially free of attachment one to another over the entire length from inner face attachment point 63 to the point of attachment about second elastic element 64. Fluids which would otherwise tend to leak through breathable portion 45 tend to be trapped in the space between outer face section 61 and inner face section 62.

Figure 7:
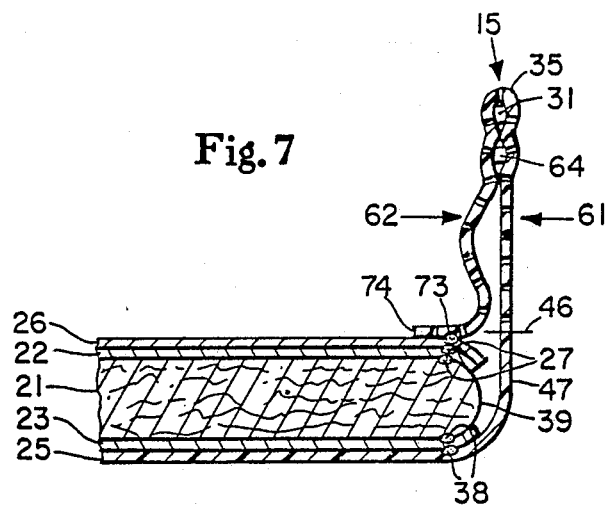
FIG. 7 is a cross sectional view of an alternate embodiment of the present invention taken along a line corresponding to line 3—3 of FIG. 1.

An alternate embodiment of cuff 15 is illustrated in FIG. 7, which is, as are FIGS. 3 through 6, a cross section of generalized cuff 15 of disposable diaper 10 of FIG. 1 taken along line 3—3. This embodiment differs from that shown in FIG. 6 in that that portion of apertured film which forms inner face section 62 of cuff 15 is attached to topsheet 26 at inner attachment point 73 by means known to those skilled in the art, such as adhesive attachment. Inner attachment point 73 is spaced some finite distance (as from about 3 to about 25 millimeters) inwardly from longitudinal side margin 39 of absorbent core 21. Inner face section 62 terminates at free end 74. Optionally, the inner face section can be secured to topsheet 26 over essentially the entire distance from inner face attachment point 73 to free end 74 by means known to those skilled in the art. Further, backsheet 25 and cuff 15 are essentially free of attachment to other parts of the disposable diaper (except the elastic elements) over the distance from optional securement means 38 to inner face attachment point 73. Inner face section 62 and outer face section 61 are likewise essentially free of attachment one to another over the same region.

In the embodiments discussed and described above, the cuffs were formed either by a separate element or by an extension of the backsheet. The cuff can be formed by an extension of the topsheet in manners analogous to those shown; such embodiments are not disclaimed.

Figure 10:
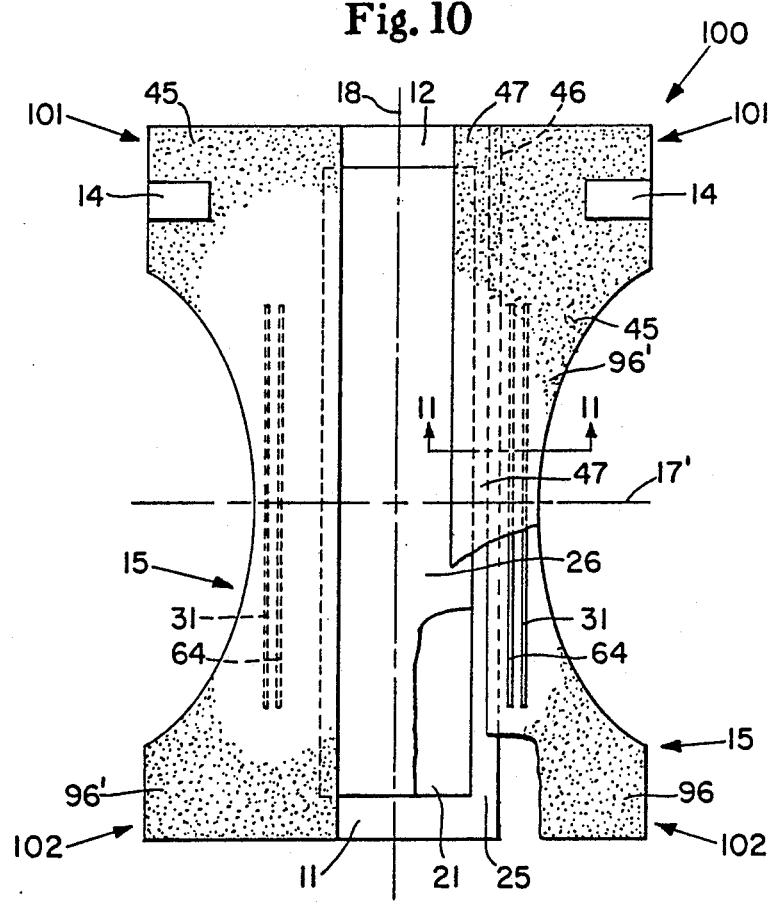
FIG. 10 is a plan view of a disposable diaper in unfolded configuration and using the present invention.
Figure 11:
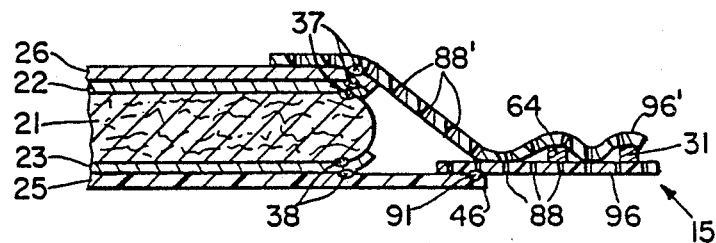
FIG. 11 is a cross sectional view of the diaper of FIG. 10 taken along line 11—11.

As noted above, the present invention has been described in detail as applied to the Aziz and Blaney diaper; it also finds utility in other disposable diaper embodiments such as that described by Buell. FIGS. 10 and 11 generally illustrate its application in diapers having a contoured configuration in diapers as described by Buell.

In FIG. 10, disposable diaper 100 is shown unfolded in plan view. The figure is somewhat simplified for clarity; for example, certain details to the left of longitudinal center line 18 have been omitted. FIG. 11 is a cross sectional view of a portion of disposable diaper 100 taken along line 11—11 of FIG. 10; the relative thicknesses of some elements have been exaggerated for clarity.

Disposable diaper 100 is generally contoured in configuration. It is symmetrical about longitudinal center line 18. Lateral central line 17' is displaced away from back waist portion 12 and toward front waist portion 11 for improved fit. Cuffs 15 comprise breathable portion 45 and impermeable portion 47 separated by an imaginery line of demarcation 46. It should be noted that in FIGS. 10 and 11, imaginery line of demarcation 46 in each cuff corresponds with the longitudinal edge of backsheet 25.

Disposable diaper 100 comprises absorbent core 21, backsheet 25, and topsheet 26. (In FIG. 10, topsheet 26, breathable cuff sub-element 96, and upper breathable cuff sub-element 96' are shown partially cut away for clarity.) In the particular embodiment illustrated, disposable diaper 100 has elastic element 31 and second elastic element 64 in each cuff 15. The elastic elements are affixed to disposable diaper 100 in such a manner that they tend to elastically contract the disposable diaper when it is in contacting relationship with the legs of the infant to which it is applied. Absorbent core 21 has associated with it top envelope tissue 22 and back envelope tissue 23 which are not shown in FIG. 10. Topsheet 26, top envelope tissue 22, absorbent core 21 and back envelope tissue 23 are secured together by securement means 37 and optional securement means 38. Adhesive attachment tapes 14 are fixed to disposable diaper 100 by adhesive means not shown.

Cuff 15 of disposable diaper 100 is formed generally as illustrated in FIG. 9. That is, breathable cuff sub-element 96, which is provided with apertures 88, is affixed in lapping relationship to backsheet 25 by securement means 91. Breathable cuff sub-element 96 is affixed to elastic element 31 and second elastic element 64 by adhesive securement means not shown. As illustrated, cuff 15 comprises breathable cuff sub-element 96 and upper breathable cuff sub-element 96'. The fact that the breathable portions of cuff 15 comprise two elements in the embodiment illustrated is an artifact of construction. The most efficient way to construct disposable diaper 100 is to use a unitary apertured film which is, during manufacture, folded over and about elastic elements 31 and 64 and secured thereto. Later in the manufacturing process, the side margin of the folded apertured film is cut away along the longitudinal side of the disposable diaper to form the contoured configuration thereby leaving the apertured film in two parts: breathable cuff sub-element 96 and upper breathable cuff sub-element 96'. Upper breathable cuff sub-element 96', which is provided with apertures 88', is affixed to elastic element 31 and second elastic element 64 (and, consequently, to breathable cuff sub-element 96) by adhesive securement means not shown and to topsheet 26 by securement means 37.

Disposable diaper 100 comprises rear waist side extensions 101 and front waist side extentions 102 which, in the embodiment illustrated, are breathable (permeable to vapor) outboard of imaginery line of demarcation 46. The breathable portions of waist side extensions 101 and 102 occupy essentially the entire area of waist side extensions 101 and 102. It is possible, and preferred in certain circumstances, to provide disposable diaper 100 with an absorbent core having a shape similar to that of the overall diaper rather than the rectangular shape illustrated in FIG. 10. In such an event, the overall breathable area of waist side extensions 101 and 102 will be reduced by the intrusion of the waist side extensions of the shaped abosrbent core.

In the discussion above of the present invention, the absorbent device involved has been assumed to be a diaper intended for use by infants. It is within the contemplation of the inventor that the present invention can be used in an analogous manner for diapers or briefs intended for use by incontinent persons other than infants, such as incontinent adults. Further, the present invention has been described in terms of disposable diapers having elasticized cuffs and generally rectangular absorbent cores. It is within the contemplation of the inventor that the present invention will find utility with disposable diapers and the like having non-elasticized cuffs (although such use is not preferred) and with absorbent cores having shapes other than rectangular. Still further, while specific construction details and techniques have been illustrated, it is anticipated that other construction details and techniques can be used without departing from the spirit and the scope of the present invention.

While the preferred use of the present invention is with disposable absorbent products such as disposable diapers, the teachings of the invention can also be applied to disposable briefs such as disposable panties.

In order to better illustrate the present invention, and not by way of limitation, the following example is presented.

EXAMPLE

Disposable diapers utilizing the present invention were constructed according to the teachings of this specification. When completed, the disposable diapers were as illustrated in FIG. 1. The construction details in the front and rear waist areas were as illustrated in FIG. 2. The cuffs were constructed as illustrated in FIG. 7. The breathable and impermeable portions of the cuffs were obtained by joining apertured thermoplastic film to unapertured thermoplastic film in the manner shown in FIG. 9.

The absorbent core (21) of each disposable diaper was an airlaid batt of comminuted wood pulp fibers. The batt was about 25.4 centimeters (cm) wide and about 40.0 cm long. It was about 0.3 cm thick and weighed from about 46 to about 54 grams (g).

Envelope tissues were tissue paper made using polyacrylamide wet-strength resin having a basis weight of about 19.5 g per square meter (M). The top envelope tissue (22) was about 45 cm long (before assembly) and about 25.4 cm wide while the back envelope tissue (23) was about 44 cm long (before assembly) and about 25.4 cm wide. The envelope tissues were assembled about the absorbent core as shown in FIGS. 2 and 7.

In the disposable diaper of this example, the topsheet (26) was the non-woven, polypropylene fabric previously described and was about 45 cm by 25.4 cm before assembly. It, too, was assembled about the absorbent core as shown in FIGS. 2 and 7.

The backsheet (25) and the impermeable portion (47) of the cuff (15) were constructed from matt-finish, unapertured polyethylene film having a thickness of 0.025 mm. The breathable portion (45) of each cuff was constructed from apertured polyethylene which was attached to the unapertured polyethylene as shown in FIG. 9. Two 45 cm long by about 6 cm wide strips of apertured polyethylene were attached to a 45 cm long by 26 cm wide rectangle of unapertured polyethylene, one along either longitudinal edge, to form a composite backsheet which functions as an integral backsheet. Adhesive attachment with NS 34-2857 adhesive as made by National Starch & Chemical Company of Plainfield, N.J. was used.

The apertured polyethylene film was formed from a 0.025 mm thick film. Apertures were selectively formed in the film in a hexagonal array having an aperture at each corner and having one additional aperture located at the center of each hexagon. There were about 90 apertures per square centimeter. Each aperture approximated the form of a truncated cone having a height of about 0.40 mm with average apex and base opening diameters of 0.38 mm and 0.56 mm, respectively. Spacing between individual apertures varied from about 1.14 mm to about 1.91 mm between centers. The apertured film had an open area of about 7%. The truncated cones were oriented so that the apices were inside the loop forming the cuff. In addition, the entire surface of the apertured film was textured to decrease surface gloss and film rigidity.

The elastic elements (31 and 64) were 0.24 cm wide by 0.02 cm thick Fulflex 9211 bands each about 22.2 cm long prior to attachment. They were attached to the cuffs by hot melt adhesive while the bands were in the stretched condition.

In each cuff, the second elastic element (64) was secured to the composite backsheet so that the second elastic element centerline was about 1.6 cm from the longitudinal side margin (39) of the absorbent core when in the plane of the outer (rear) surface of the core. The elastic element (31) was secured to the composite backsheet so that the centerlines of the two elastic elements were about 0.95 cm apart. In this construction, the unapertured portion of the backsheet extended to within about 0.6 cm of the centerline of the second elastic element. Thus, the junction between apertured and unapertured sections fell between the longitudinal side margin of the absorbent core and the second elastic element; this junction corresponded to the imaginary line of demarcation (46).

The backsheet (and the back envelope tissue) were attached to the absorbent core by an optional securement means (38) comprising a bead of NS 34-2857 adhesive running essentially the entire longitudinal length of the absorbent core and spaced about 0.95 cm from its longitudinal side margin.

The apertured inner faces (62) of the cuffs were attached to the topsheet (and indirectly to the top envelope tissue and the absorbent core) at an inner face attachment point (73) by a bead of NS 34-2857 adhesive running essentially the entire longitudinal length of the disposable diaper. (In the front and rear waist portions, ((11 and 12)), the apertured film was attached directly to the unapertured film.) The adhesive bead was spaced about 0.6 cm from the longitudinal side margin of the absorbent core. The inner face portion (62) terminated at a free end (74) spaced about 0.6 cm from the inner face attachment point and nearer the diaper longitudinal centerline.

The overall width of the cuff from the longitudinal margin of the absorbent core to the distal edge (35) of the cuff (when the cuff and the absorbent pad are so oriented that the absorbent pad was essentially planar and the cuff was essentially in the plane of the outer or back face of the absorbent core) was about 2.9 cm, of which about the outer 1.9 cm constituted the breathable portion.

When worn by infants, it appeared that the disposable diaper of this example was comfortable, absorbed and contained discharged body fluids, protected the infants' skin and surroundings from discharged body fluids, and was cooler and self-dried to a greater extent than did similar disposable diapers not using the present invention.

What is claimed is:

1. A disposable diaper comprising:
   a liquid impermeable backsheet;
   a liquid pervious topsheet secured to said backsheet;
   an absorbent element interposed between said topsheet and said backsheet;
   a longitudinally extending breathable cuff positioned in each longitudinal side margin of the diaper, each of said cuffs having a fixed edge and a distal edge spaced from said fixed edge, each of said cuffs having said fixed edge attached to the diaper, said distal edge being unsecured to at least a portion of the diaper, wherein each of said cuffs is permeable to vapor over at least a portion of its extent; and
   an elastic element operatively associated with said distal edge of each of said cuffs and affixed in an elastically contractable condition to said cuff to render said distal edge of said cuff elastically contractable so that said elastic element effectively contracts or gathers the cuff material adjacent said elastic element so that said distal edge is displaced inwardly from said absorbent element and said fixed edge.

2. The disposable diaper of claim 1 wherein each of said fixed edges is attached to said backsheet.

3. The disposable diaper of claim 2 wherein said cuffs are each formed by a separate element affixed to said backsheet.

4. The disposable diaper of claim 2 wherein said cuffs are each formed unitarily with said backsheet.

5. The disposable diaper of claim 1 wherein each of said fixed edges is attached to said topsheet.

6. The disposable diaper of claim 5 wherein said cuffs are each formed unitarily with said topsheet.

7. The disposable diaper of claim 5 wherein said cuffs are each formed by a separate element affixed to said topsheet.

8. The disposable diaper of claim 1 additionally comprising a second elastic element operatively associated with each of said cuffs.

9. The disposable diaper of claim 1 wherein said elastic element comprises one or several elastic elements.

10. The disposable diaper of claim 1 wherein said cuffs are vapor and liquid permeable.

11. The disposable diaper of claim 1 wherein said cuffs are vapor permeable but liquid impermeable, said cuffs being more permeable to vapor than said backsheet.

12. The disposable diaper of claim 1 wherein said cuff comprises a vapor permeable portion and a vapor impermeable portion.

13. A disposable diaper comprising:
    a liquid impermeable backsheet;
    a liquid pervious topsheet secured to said backsheet;
    an absorbent element interposed between said topsheet and said backsheet;
    a longitudinally extending breathable cuff positioned in each longitudinal side margin of the diaper, each of said cuffs having a fixed edge and a distal edge spaced from said fixed edge, each of said cuffs having said fixed edge attached to the diaper, said distal edge being unsecured to at least a portion of the diaper, wherein each of said cuffs is permeable to vapor over at least a portion of its extent such that each of said cuffs comprises a vapor permeable portion and a vapor impermeable portion, said vapor permeable portion being positioned adjacent said distal edge and said vapor impermeable portion being positioned intermediate said vapor permeable portion and said fixed edge; and
    an elastic element operatively associated with said distal edge of each of said cuffs and affixed in an elastically contractable condition to said cuff to render said distal edge of said cuff elastically contractable so that said elastic element effectively contracts or gathers the cuff material adjacent said elastic element so that said distal edge is displaced inwardly from said absorbent element and said fixed edge.

14. The disposable diaper of claim 12 wherein said vapor permeable portion comprises from about 5% to about 75% of said cuff.

15. The disposable diaper of claim 1 wherein said cuff comprises thermoplastic film provided with apertures.

16. The disposable diaper of claim 15 wherein said thermoplastic film has a dimensionless R value of between about 2 to about 40.

17. The disposable diaper of claim 1 wherein said cuff comprises non-woven fabric.

18. A disposable diaper having a front waist portion, a back waist portion, and a crotch portion placed between said front waist portion and said back waist portion, the diaper comprising:
    a liquid impermeable backsheet;
    a liquid pervious topsheet secured to said backsheet;
    an absorbent element interposed between said topsheet and said backsheet;
    a longitudinally extending breathable cuff positioned in each longitudinal side margin of the diaper in at least the crotch portion, each of said cuffs having a fixed edge and a distal edge spaced from said fixed edge, each of said cuffs having said fixed edge attached to the diaper, said distal edge being unsecured to at least a portion of the diaper, each of said cuffs formed by a separate element affixed to the diaper, each of said cuffs having a vapor permeable portion and a vapor impermeable portion so that each of said cuffs is permeable to vapor over at least a portion of its extent; and an elastic element operatively associated with said distal edge of each of said cuffs and affixed in an elastically contractable condition to said cuff to render said distal edge of said cuff elastically contractable so that said elastic element effectively contracts or gathers the cuff material adjacent said elastic element so that said distal edge is displaced inwardly from said absorbent element and said fixed edge.

19. A disposable diaper comprising:

a liquid impermeable backsheet;

a liquid pervious topsheet secured to said backsheet;

an absorbent element interposed between said topsheet and said backsheet;

a longitudinally extending breathable cuff positioned in each longitudinal side margin of the diaper in at least the crotch portion, each of said cuffs having a fixed edge and a distal edge spaced from said fixed edge, each of said cuffs having said fixed edge attached to the diaper, said distal edge being unsecured to at least a portion of the diaper, each of said cuffs formed by a separate element affixed to the diaper, each of said cuffs having a vapor permeable portion and a vapor impermeable portion so that each of said cuffs is permeable to vapor over at least a portion of its extent, said vapor permeable portion being positioned adjacent said distal edge and said vapor impermeable portion being disposed intermediate said vapor permeable portion and said fixed edge; and an elastic element operatively associated with said distal edge of each of said cuffs and affixed in an elastically contractable condition to said cuff to render said distal edge of said cuff elastically contractable so that said elastic element effectively contracts or gathers the cuff material adjacent said elastic element so that said distal edge is displaced inwardly from said absorbent element and said fixed edge.

20. The disposable diaper of claim 19 wherein said vapor permeable portion comprises from about 5% to about 75% of said cuff.

21. The disposable diaper of claim 20 wherein said vapor permeable portion comprises from about 5% to about 75% of the width of said cuff.

22. The disposable diaper of claim 21 wherein said cuff comprises thermoplastic film provided with apertures.

23. The disposable diaper of claim 22 wherein said elastic element comprises one or several elastic elements.

24. The disposable diaper of claim 23 wherein said cuffs extend the entire length of the diaper.

25. The disposable diaper of claim 24 wherein said vapor permeable portion is vapor permeable but liquid impermeable, said cuffs being more permeable to vapor than said backsheet.

26. The disposable diaper of claim 25 wherein the longitudinal side margins of the diaper are contoured such that they are non-linear over at least a portion of their respective lengths.

27. The disposable diaper of claim 26 wherein said absorbent element comprises super absorbent polymers.

28. The disposable diaper of claim 27 wherein said cuffs are each positioned adjacent the longitudinal side margin of said absorbent element in at least the crotch portion.

29. The disposable diaper of claim 28 wherein said fixed edge is affixed to said topsheet.

30. The disposable diaper of claim 29 wherein said thermoplastic film has a dimensionless R value of between about 2 and about 40.

31. A disposable diaper having a front waist portion, a back waist portion, and a crotch portion placed between said front waist portion and said back waist portion, the diaper comprising:

a liquid impermeable backsheet;

a liquid pervious topsheet secured to said backsheet;

an absorbent element interposed between said topsheet and said backsheet, said absorbent element having longitudinal side margins;

two longitudinally extending breathable cuffs, said cuffs each comprising a side flap extending outwardly from and along each longitudinal side margin of said absorbent element in at least the crotch portion, each of said side flaps having an outer surface, an inner surface, and a distal edge spaced from said longitudinal side margin of said absorbent element and forming the longitudinal side margin of the diaper, each of said side flaps having a vapor permeable portion positioned adjacent said distal edge and a vapor impermeable portion positioned intermediate said vapor permeable portion and said longitudinal side margin of said absorbent element, said outer surface of said side flap constructed essentially of an integral film material with said backsheet such that said permeable portion is formed of an apertured portion of said film material and said vapor impermeable portion is formed of said backsheet, said vapor permeable portion being more permeable to vapor than said backsheet, and an elastic member operatively associated with said side flap in an elastically contractable condition, the elastic member being effective to gather the side flap.

32. The disposable diaper of claim 31 wherein said elastic member is positioned 1.6 centimeters from said absorbent element.

* * * * *